US010874637B2

(12) United States Patent
Rötig et al.

(10) Patent No.: US 10,874,637 B2
(45) Date of Patent: Dec. 29, 2020

(54) METHODS AND PHARMACEUTICAL COMPOSITIONS FOR THE TREATMENT OF NEURODEGENERATION WITH BRAIN IRON ACCUMULATION

(71) Applicants: INSERM (Institut National de la Santé et de la Recherche Médicale), Paris (FR); Université Paris Descartes, Paris (FR); Fondation Imagine, Paris (FR); Assistance Publique-Hôpitaux de Paris (APHP), Paris (FR)

(72) Inventors: Anne Agnès Rötig, Paris (FR); Anthony Drecourt, Paris (FR)

(73) Assignees: INSERM (INSTITUT NATIONAL DE LA SANTE ET DE LA RECHERCHE MÉDICALE), Paris (FR); UNIVERSITÉ PARIS DESCARTES, Paris (FR); FONDATION IMAGING, Paris (FR); ASSISTANCE PUBLIQUE-HÔPITAUX DE PARIS (APHP), Paris (FR)

( * ) Notice: Subject to any disclaimer, the term of this patent is extended or adjusted under 35 U.S.C. 154(b) by 0 days.

(21) Appl. No.: 16/471,307

(22) PCT Filed: Dec. 19, 2017

(86) PCT No.: PCT/EP2017/083642
§ 371 (c)(1),
(2) Date: Jun. 19, 2019

(87) PCT Pub. No.: WO2018/115012
PCT Pub. Date: Jun. 28, 2018

(65) Prior Publication Data
US 2020/0113868 A1 Apr. 16, 2020

(30) Foreign Application Priority Data
Dec. 20, 2016 (EP) .................................. 16306740

(51) Int. Cl.
*A61K 31/357* (2006.01)
*A61P 25/28* (2006.01)
(52) U.S. Cl.
CPC ............ *A61K 31/357* (2013.01); *A61P 25/28* (2018.01)
(58) Field of Classification Search
CPC ........ A61K 31/00; A61K 31/357; A61P 25/28
See application file for complete search history.

(56) References Cited

U.S. PATENT DOCUMENTS

| 9,999,621 | B2 * | 6/2018 | Li ....................... A61K 31/4748 |
| 2013/0012470 | A1 * | 1/2013 | Colman ................. A61K 45/06 |
| | | | 514/54 |
| 2013/0028882 | A1 * | 1/2013 | Colman ............... A61K 31/731 |
| | | | 424/94.61 |
| 2015/0093371 | A1 * | 4/2015 | Colman ............... A61K 36/185 |
| | | | 424/94.61 |

FOREIGN PATENT DOCUMENTS

| WO | 2008/046109 A2 | 4/2008 |
| WO | 2008/046109 A3 | 4/2008 |

OTHER PUBLICATIONS

Drecourt et al., "Impaired Transferrin Receptor Palmitoylation and Recycling in Neurodegeneration with Brain Iron Accumulation", 2018, The American Journal of Human Genetics, 102(2), pp. 266-277. (Year: 2018).*
Qian Ba et al.; "Dihydroartemisinin Exerts Its Anticancer Activity through Depleting Cellular Iron via Transferrin Receptor-1"; PLOS One, vol. 7, No. 8, Aug. 10, 2012, p. e42703.
Kumar et al.; "Neuroferritinopathy: Pathophysiology, Presentation, Differential Diagnoses and Management"; retrieved from the internet— www.tremorjournal.org, Mar. 8, 2016, the whole document.
Swaiman: "Hallervorden-Spatz syndrome and brain iron metabolism"; Archives of Neurology, vol. 48, No. 12, Dec. 1, 1991, pp. 1285-1293.

* cited by examiner

*Primary Examiner* — My-Chau T. Tran
(74) *Attorney, Agent, or Firm* — W&C IP

(57) ABSTRACT

The present invention relates to methods and pharmaceutical compositions for the treatment of neurodegeneration in with brain iron accumulation (NBIA). Studying two novel genes, namely, CRAT encoding the carnitine acetyltransferase and REPS1 involved in endocytosis and vesicle transport, and a series of known NBIA genes, the inventors reported on iron overload related to increased levels and abnormal recycling of transferrin receptor as a common feature in NBIA. They ascribe this anomaly, at least in part, to impaired palmitoylation of the receptor as a common consequence of the various disease causing mutations. Finally, the inventors show that Artesunate improved TfR1 palmitoylation in NBIA fibroblasts. In particular, the present invention relates to a method of treating neurodegeneration with brain iron accumulation in a subject in need thereof comprising administering to the subject a therapeutically effective amount of a drug increasing TfR1 palmitoylation.

4 Claims, 1 Drawing Sheet

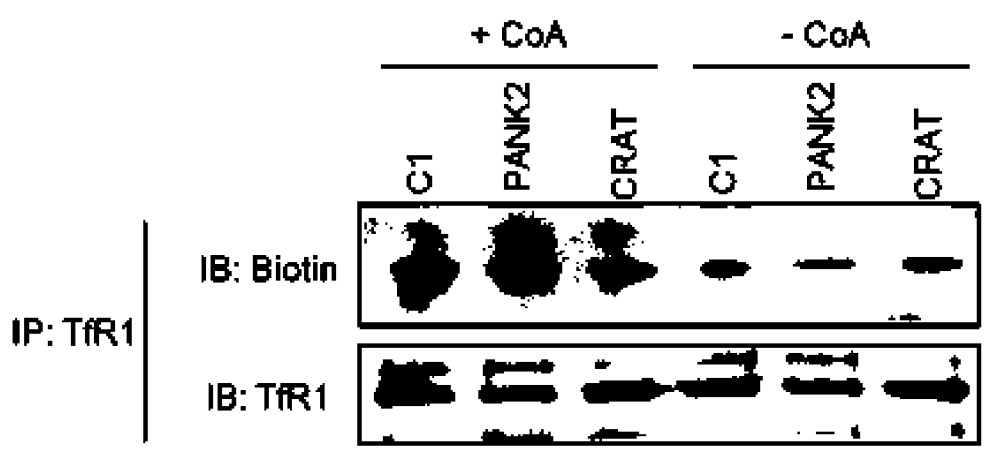

METHODS AND PHARMACEUTICAL COMPOSITIONS FOR THE TREATMENT OF NEURODEGENERATION WITH BRAIN IRON ACCUMULATION

FIELD OF THE INVENTION

The present invention relates to methods and pharmaceutical compositions for the treatment of neurodegeneration with brain iron accumulation (NBIA).

BACKGROUND OF THE INVENTION

Neurodegeneration with brain iron accumulation (NBIA) is a genetically heterogeneous condition causing progressive extrapyramidal dysfunction with dystonia, rigidity, choreoathetosis and brain MRI evidence of divalent metal accumulation in brain. Eleven disease genes have been hitherto identified$_1$ (PANK2, PLA2G6, COASY, FA2H, ATP13A2, C2orf37, WDR45, C19ORFf12, CP, FTL and GTPBP2$_2$), PLA2G6 which causes neuroaxonal dystrophy and PANK2 being the prevalent disease genes. Yet, only two NBIA genes are clearly related to iron metabolism, namely FTL encoding the light subunit of ferritin, the major intracellular iron storage protein, and CP encoding ceruloplasmin. How other NBIA genes are related to iron metabolism remains poorly understood.

On the other hand, internalization of transferrin-bound iron by transferrin receptor 1 (TfR1)-mediated endocytosis is the major route of iron uptake$_3$. In living cells, newly imported iron is incorporated into ferritin, a multimeric protein made up of two subunits, H-ferritin and L-ferritin. Homeostasis of cellular iron is regulated by a post-transcriptional mechanism involving iron responsive proteins (IRPs) which represent the main iron regulators in vertebrates. In human, cytosolic aconitase (ACO1) is converted into IRP (IRP1) when cytosolic iron declines. Another IRP devoid of aconitase activity, IRP2, is primarily regulated by iron-dependent degradation. IRPs bind to the 3'UTR of transferrin receptor mRNA, protecting it against rapid degradation and allowing cells to import more iron by endocytosis of transferrin (Tf). IRPs also bind the 5'UTR of ferritin mRNAs, hampering ferritin synthesis. In high iron conditions, IRP1 is converted into aconitase and IRP2 is degraded, allowing iron storage and limiting iron entry. Up till now, this post-transcriptional level of regulation was the only mechanism known to regulate TfR1 and ferritin.

SUMMARY OF THE INVENTION

The present invention relates to methods and pharmaceutical compositions for the treatment of neurodegeneration with brain iron accumulation (NBIA). In particular, the present invention is defined by the claims.

DETAILED DESCRIPTION OF THE INVENTION

Studying two novel genes, namely, CRAT encoding the carnitine acetyltransferase and REPS1 involved in endocytosis and vesicle transport, and a series of known NBIA genes, the inventors report here on iron overload related to increased levels and abnormal recycling of transferrin receptor as a common feature in NBIA. They ascribe this anomaly, at least in part, to impaired palmitoylation of the receptor as a common consequence of the various disease causing mutations. Finally, the inventors show that Artesunate improved TfR1 palmitoylation in NBIA fibroblasts.

Accordingly the first object of the present invention relates to a method of treating neurodegeneration with brain iron accumulation in a subject in need thereof comprising administering to the subject a therapeutically effective amount of a drug increasing TfR1 palmitoylation.

As used herein the expression "neurodegeneration with brain iron accumulation" or "NBIA" has its general meaning in the art and refers to a group of rare, genetic neurological disorders characterized by abnormal accumulation of iron in the basal ganglia. The hallmark clinical manifestations of NBIA relate to the body's muscle function and feature a progressive movement disorder, including dystonia, choreoathetosis, stiffness in the arms and legs and Parkinsonism. Most forms of NBIA involve eye disease. The most common problems are degeneration of the retina and optic atrophy. A general loss of brain cells and tissue also are frequently observed, conditions called cerebral atrophy and cerebellar atrophy. Onset of NBIA ranges from infancy to adulthood. Progression can be rapid or slow with long periods of stability. In some embodiments, the NBIA results from a disease gene selected from PANK2, PLA2G6, COASY, FA2H, ATP13A2, C2orf37, WDR45, C19ORFf12, CP, FTL, GTPBP2, CRAT and REPS1. In some embodiments, the NBIA is pantothenic kinase-associated neurodegeneration, infantile neuroaxonal dystrophy, atypical neuroaxonal dystrophy, mitochondrial-membrane protein-associated neurodegeneration, beta-propeller protein-associated neurodegeneration, aceruloplasminemia, fatty acid hydroxylase-associated neurodegeneration, neuroferritinopathy, Woodhouse-Sakati syndrome, or coasy protein-associated neurodegeneration.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

In some embodiments, the drug is artesunate. As used herein, the term "artesunate" has its general meaning in the art and refers to (3R,5aS,6R,8aS,9R,10S,12R,12aR)-Decahydro-3,6,9-trimethyl-3,12-epoxy-12H-pyrano [4,3-j]-1,2-benzodioxepin-10-ol, hydrogen succinate. The term encompasses any of the individual enantiomers of artesunate. In particular, the term may refer to just a single enantiomer, or a racemic or non-racemic mixture of the enantiomers. The term also includes polymorphs and hydrates of artesunate. The term also includes salts and esters of artesunate. The term also includes prodrugs of artesunate, and enantiomers, racemic mixtures, non-racemic mixtures, polymorphs, hydrates, salts and esters of said prodrugs.

By a "therapeutically effective amount" of the drug as above described is meant a sufficient amount to provide a therapeutic effect. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

According to the invention, the drug is administered to the subject in the form of a pharmaceutical composition. Typically, the drug may be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semisolid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The drug can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, or calcium, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURE

FIG. 1: Iron content and regulation of iron homeostasis in fibroblasts of NBIA subjects. Effect of CoA supplementation on TfR1 palmitoylation in PANK2 and CRAT fibroblasts. Fibroblasts were treated with or without CoA 25 µM for 72 h, and TfR1 protein was immunoprecipitated with mouse anti-TfR1 antibody to perform the palmitoylation assay. In each condition, the upper panel shows the palmitoylated TfR1 level (IB: Biotin) and the immunoprecipitated amount of TfR1 (IB: TfR1).

EXAMPLE 1

Material & Methods
Patients

Patient 1, a girl born to first cousin Turkish parents after a term pregnancy and normal delivery (birth weight: 3.5 Kg, height: 51 cm, OFC: 35 cm) walked aged 14 mths but soon developed speech delay first ascribed to a mild hearing loss. Imbalanced gait and slowly progressive cerebellar ataxia were noted at 3 yrs. She gradually lost the ability to stand, walk and write. Tremor, dysmetry, hypotonia, brisk deep tendon reflexes and sensory neuropathy were suggestive of a slow progressive spinocerebellar degeneration. Brain MRI showed evidence of cerebellar atrophy, posterior leukodystrophy. Hyperintensity of basal ganglia and hypointensity of globus pallidum and substancia nigra on T2* sequences were suggestive of major iron accumulation (FIG. 7).

Patient 2, the third child of unrelated healthy parents of French origin (birth weight: 2.6 Kg, height: 46.5 cm, OFC: 33.5 cm) had speech and motor delay. She walked alone aged 18 mths but developed progressive cerebellar ataxia and pyramidal syndrome and loosed the ability of walk aged 9 yrs. At that age, nystagmus, dysarthria, dysmetry, spasticity of the inferior limbs and pes cavus were noted. Skeletal muscle biopsy revealed negative SDH and COX staining in numerous fibers but metabolic workup and mitochondrial respiratory chain enzyme activities were normal. Brain MRI showed progressive cerebellar and cerebral atrophy and T2* evidence of brain iron accumulation in pallidi and pedoncules. She passed away aged 20 yrs after a 10 yr gradual worsening of her condition (FIG. 7).

Patient 3, the sister of patient 2, had a similar, yet slightly milder clinical course. Aged 14 yrs, she can still walk with aid, hold a pencil and practice indoor bike and swimming.

Interestingly, the parents mentioned some fluctuations in their neurological conditions and a significant worsening following monthly menstruations in patients 2-3.

Informed consent for diagnostic and research studies was obtained for all subjects in accordance with the Declaration of Helsinki protocols and approved by local Institutional Review Boards in Paris.

Exome Sequencing

Exome sequencing was performed on genomic DNA (1 µg) isolated from blood leukocytes. Exons were captured by the in-solution enrichment methodology (SureSelect Human All Exon Kits Version 3, Agilent, Massy, France) using the company's biotinylated oligonucleotide probe library (Human All Exon v3 50 Mb, Agilent). Each genomic DNA was then sequenced on a sequencer as paired-end 75 bases (Illumina HISEQ2000, Illumina, San Diego, USA). Image analyses and base calling were performed with Real Time Analysis (RTA) Pipeline version 1.9 with default parameters (Illumina). Sequences were aligned to the human genome reference sequence (hg19 assembly), SNPs were called on the basis of the allele calls and read depth using the CASAVA pipeline (Consensus Assessment of Sequence and Variation 1.8, Illumina). Known SNPs reported in dbSNP, 1000 genomes, Exome Variant Server and in house SNP database were excluded as well as intergenic, non-coding RNA and UTR variants.

Cell Culture

Skin fibroblasts were isolated from patients 1-2 and from four NBIA patients carrying biallelic PANK2, PLA2G6, C19ORF12 and FA2H mutations (Supplementary Table 2). Fibroblasts were grown in DMEM (Life technologies) medium supplemented with 10% fetal beef serum (FBS), 2 mM L-glutamine, 2.5 mM pyruvate, 100 µg/ml streptomycin, 100 U/ml penicillin at 37° C. For treatment with ferric ammonium citrate (FAC), 90% confluent cells were incubated for 72 h with or without 100 µM FAC in serum-free DMEM (i.e. Tf free). HeLa cells were grown in the same medium.

Modeling of the Human CRAT Mutation

The 1.6 Å coordinate set for the human CRAT (pdb code: 1 nm8) was used to map the Arg321 residue. Swiss-Pdb Viewer 3.7 (http://www.expasy.org/spdbv) was used to analyze the structural insight into CRAT mutation and visualize the structures.

β-Oxidation of Palmitoyl-CoA

Cells seeded in 6-well plates were incubated when confluent with 250 µM $^{13}$C16-labelled palmitate, fatty acid-free bovine serum albumin (molar ratio palmitate/albumin: 4/1) and 0.4 mmol/L carnitine for 6 h. Cells were removed by trypsinization and after washing with PBS stored at −80° C. until analysis. For acylcarnitine analysis, pellets were resuspended in 60 µL deionized water and briefly sonicated. Mixed internal standards (20 µl of 20 µM $^2$H$_9$-L-carnitine, 4 µM $^2$H$_3$ octanoylcarnitine, 1 µM $^2$H$_3$ octadecanoylcarnitine) were added to 45 µL of cell homogenate. Proteins were precipitated by addition of 400 µL ethanol and supernatant was extracted twice with 400 µL hexane. The aqueous layer was transferred in a vial, dried under nitrogen and reconstituted with 100 µL acetonitrile/water (1:1 v/v, 0.025% formic acid). Acylcarnitines were analyzed on a API 3000 (Applied Biosystem) triple quadripole mass spectrometer, detecting precursors of m/z 85 and quantified by comparison to deuterated internal standards. Proteins were measured by Lowry method.

Western Blot

Cultured skin fibroblasts or HeLa cells were harvested on ice by scraping in reducing or non-reducing cell lysis buffer. SDS-PAGE was performed on whole-cell protein extracts. Immunodetections were performed in PBS with 5% milk, 0.05 Tween20 (SIGMA) using the following antibodies: rabbit anti-CRAT (HPA022815, Sigma), rabbit anti-ACOT8 (SAB4500009 SIGMA), mouse anti-REPS1 (ab69221), mouse anti-SOD1 (ab86454), mouse anti-TfR1 (Zymed 136890), rabbit anti-ferritin (ab75973), rabbit anti-IRP1 (ab126595), rabbit anti-IRP2 (ab80339), mouse anti-GRIM19 (ab110240), rabbit anti-catalase (ab16731), rabbit anti-FBXLS (ab140175), rabbit anti-LC3B (ab51520) and mouse anti-actin antibodies (ab8226). HRP-conjugated goat anti-mouse IgG H&L (ab6789) or goat anti mouse IgG H&L antibodies (ab6789) were used as secondary antibodies before ECL-based detection (SuperSignal® West Dura, Thermo Scientific). Images were visualized and treated using a CCD camera (BioRad) and ImageLab software (BioRad).

Detection of carbonyl groups was performed using OxyBlot Protein Oxidation Detection Kit (S7150 Chemicon) according to recommendations of the manufacturer.

Knock-Down of CRAT and ACOT8

HeLa cells were plated at 80% confluence in 6 well plates the day before transfection. Cells were transfected with Dharmafect 1 (Dharmacon) and 50 nM siRNA per target in 10% FBS antibiotic-free OPTIMEM as recommended by the manufacturer. Palmitoyl-CoA β-oxidation and Western blot were performed two days post-transfection. siRNA purchased from Dharmacon were as follows: human CRAT siRNA (ON-TARGETplus SMARTpool L-009524-00-0005), human ACOT8 siRNA (ON-TARGETplus SMARTpool L-009600-01-0005), and human non targeting pool siRNA (ON-TARGETplus Non-targeting Pool).

Overexpression of CRAT and REPS1

The CRAT or REPS1 full length cDNAs were cloned in the pLenti7.3 expression vector.

For virus production, HEK293FT cells were plated three days before transfection in DMEM supplemented with 10% of heat-inactivated FBS (Invitrogen, 10270106) at 80% confluence. HEK293FT cells were co-transfected using 30 µL of JetPRIME PolyPLUS reagents with the three packaging plasmids REV, VSVG, PAX2, and the pLenti7.3 expression vector containing either CRAT or REPS1 cDNA with a 1:3:6:10 DNA ratio. The supernatant containing the viral particles was collected every 12 h during 3 days, centrifuged at 5000 rpm for 5 min, filtered through a 0.8 µm filter and centrifuged for 2 h at 19000 rpm at 4° C. Pellets were collected and resuspended in 200 µL DMEM. The fibroblasts were then transduced at 60-70% confluence with multiplicity of infection of 5.

Quantification of TFRC Transcripts

Total RNA was extracted using the RNeasy Mini Kit (Qiagen) and DNase treated by the RNase-free DNase set (Qiagen) according to manufacturer's protocol. Concentration and purity of total RNA was assessed using the Nanodrop-8000 spectrophotometer (Thermo Fisher Scientific) before storage at −80° C. Then mRNAs were reverse transcribed from 2 µg of total RNA using High-Capacity RNA-to-cDNA Kit (Thermo Fisher Scientific) according to the manufacturer's instructions using random priming. Quantitative RT-PCR (qRT-PCR) was performed with digital droplet PCR (ddPCR) using QX200 DropletDigital PCR System (Bio-Rad Laboratories). TFRC cDNAs were amplified using specific primers. TATA box-binding protein (TBP, NM_003194) and β-glucuronidase (GUSB, NM_000181.3) were used for normalization. Primers are shown in Supplementary Table 3. Data from triplicates were analyzed on a droplet flow cytometer, QX200 Droplet Reader using Quantasoft analysis software (Bio-Rad Laboratories). TFRC expression levels were normalized to the mean copy numbers of TBP and GUSB housekeeping genes.

Iron Content and Imaging Flow Cytometry (Imagestream)

Total iron contents were measured using a ferrozine-based iron assay modified from[35]. For imaging flow cytometry, fibroblasts (1 to $2\times10^6$) were starved for one hour in FBS-free DMEM medium, treated with 5 mM EDTA for harvesting them without disrupting TfR1 located at cell surface, as trypsin does, washed 3 times with cold PBS and then labelled with anti-TfR1 antibodies (A24)[36] for 1 h on ice to avoid TfR1 internalization. In this condition only membrane-bound TfR1 is quantified. Secondary staining was performed using Alexa fluor 488 goat anti-mouse antibody for 30 min on ice. Cells were washed and stained with Hoechst for 5 min in a total volume of 50 µl and acquisitions were directly performed. Cell analysis was based on Hoechst-positive signal, allowing to select living cells. Samples were run on an Imagestream ISX mkII (Amnis Corp, Millipore, Seattle, Wash.) that combines flow cytometry with detailed cell-imaging and functional studies and a 40× magnification was used for all acquisitions. Data were acquired using the INSPIRE software (Amnis Corp) and analyzed using the IDEAS™ software (version 6.2 Amnis Corp). At least 20,000 events were collected in all experiments. Single stain controls were run for each fluorochrome used and spectral compensation was performed. Cells were gated for single cell using the area and aspect ratio of the bright field image and gated for focused cells using the gradient RMS feature. A specific mask was designed for analysis of the membrane localization of TfR1. Results were expressed as mean pixel intensity value which is the intensity normalized to surface area. Data analyses were performed using the IDEAS software (Amnis Corporation). Data were compensated using a compensation matrix generated using singly stained samples. Gated data were used to generate histograms measuring fluorescence intensity (sum of all pixels in an image) located at the plasma membrane by using specific mask. This mask was the result of a full bright field mask minus a 10 pixels erode bright mask resulting in doughnuts-like mask. Statistical analyses were performed with GraphPadPrism (version 5.0; GraphPad Software). The data were obtained from at least $2.10^4$ cells in three independent experiments and reported as a histogram of mean pixels for each samples and a mean of 3 controls. Two-tailed Student's unpaired t-tests or Mann-Whitney U-tests were used as appropriate. P values<0.001 were considered significant.

Confocal Microscopy

For Tf recycling, fibroblasts were spread at 40% confluence onto 12 well plates containing glass-slides 48 h before experiment. Cells were then starved in FBS-free DMEM media for 1 h at 37° C. Tf-RED (25 µg/mL) was then added for 30 min. Cells were washed 3 times with PBS and then incubated for 0, 5, 10 or 30 min in FBS-free DMEM media.

Finally, cells were washed in PBS and fixed in 4% cold PFA. Slides were mounted in DAPI containing Diamond Prolong mounting media (Thermofisher Scientific). Slides were examined with a confocal laser microscope (SP8 SMD). Image analysis was performed using ImageJ software. For each independent experiment, at least 30 cells were collected per slide. Each field was selected by viewing DAPI-positive staining which was used to define the nuclear region (NR). Each NR was enlarged by 10 pixels to generate the perinuclear region of interest (PNROI). PNROI masks were then applied on RED channel by the image calculator to obtain quantitative mean fluorescence particle intensity. Only particles of at least 8 pixels size were considered. Red fluorescence intensity thresholds were determined according to non-incubated Tf-RED cells. The number of cells analyzed is higher than 30 in three independent experiments. Data were analyzed with two-tailed Student's unpaired t-tests with GraphPadPrism (version 5.0; GraphPad Software). P values<0.05 were considered as significant.

For Tf and TfR1 trafficking, fibroblasts were spread at 40% confluence onto 12 well plates containing glass-slides 48 h before experiment. Cells were then starved in FBS-free DMEM media for 1 h at 37° C. Tf-RED (25 µg/mL) was then added for 30 min. Cells were washed 3 times with PBS and then incubated for 10 in FBS-free DMEM media. Finally, cells were washed in PBS and fixed in 4% cold PFA. Confocal microscopy was performed as previously described[37] using rabbit anti-Rab11A (Zymed 71-5300), mouse anti-LAMP2 (ab25631), Alexa Fluor® 488 conjugated goat anti-mouse IgG (Thermofisher A-11001), Alexa Fluor® 594 conjugated goat anti-rabbit IgG (Thermofisher A-11012) and ProLong® Diamond Antifade Mountant with DAPI (Thermofisher P36962).

Palmitoylation Assay

TfR1 palmitoylation in cultured skin fibroblasts was modified from[15]. Briefly, cells were lysed on ice in a DTT-free cell lysis buffer and endogenous TfR1 was immunoprecipitated with mouse anti-TfR1 antibody (Zymed) with protein G magnetic beads (Biorad). After washing with PBS, beads were incubated overnight with 50 mM N-ethylmaleimide (NEM) at 4° C., washed 3 times with PBS and then incubated with 1 M hydroxylamine (HA) at room temperature for 2 hours. After three washes, the beads were incubated with 50 mM HPDP-Biotin (Thermo) in dark for 2 hours. Biotin-labeled TfR1 level was determined by immunoblotting in non-reducing conditions using a goat anti-biotin antibody (Thermo) while immunoblotting with rabbit anti-TfR1 antibody (Abcam) was used as loading control.

Results:

REPS1 Mutations Result in NBIA and Iron Overload in Fibroblasts

Exome sequencing in two sibs born to unrelated parents (patients 2-3) revealed compound heterozygosity for two missense REPS1 variations (c.232G>C and c.338C>A; p.Val78Leu and p.Ala113Glu respectively) located in a highly conserved domain of the protein and predicted to be deleterious. The c.338C>A variation is a SNP (rs201191394) with a low minor allele frequency (0.0001) in European Americans. The variations co-segregated with the disease in the family and were absent from 110 NBIA patients and 200 control chromosomes. They did not alter the level of specific transcript (not shown) but significantly reduced the amount of REPS1 protein in patient's fibroblasts.

The RalBP1 and RalBP1-associated-Eps-domain-containing 1 (REPS1) proteins are two distinct proteins involved in endocytosis and vesicle transport. REPS1, an endocytic adaptor localized in clathrin-coated pits, interacts with endocytic scaffold intersectin 1 (ITSN1), one of the key players of clathrin-mediated endocytosis[7]. REPS1 is included in the Numb endocytic complex and could mediate recruitment of RalBP1 into this complex[8]. REPS1 is ubiquitously expressed[9], conserved across species and contains two Epsin 15 homology domains (EH1 and EH2) which are known to play a role in protein-protein interaction[10]. Both variants are located in the EH1 domain, a conserved region interacting with RalBP1. REPS1 also interacts with Rab11-FIP2, located on membranes of early endosomes[11]. The binding of REPS1 to Rab11-FIP2 induces the fusion of uncoated vesicles with early endosome, forming the endosome recycling compartment[12]. We hypothesized that REPS1 mutations could induce iron overload via an alteration of endosome trafficking and TfR1 recycling. Iron in cultured fibroblasts of patient 2 was quantified using a ferrozine-based colorimetric assay. Patient fibroblasts showed slightly increased iron content when grown for 3 days in fetal beef serum (FBS)-free DMEM (i.e. devoid of Tf-bound iron). Cells were then incubated with ferric ammonium citrate (FAC) a soluble source of iron used to increase cellular iron content and known to increase NTBI uptake in fibroblasts[13] by a poorly understood way that could occur via endocytic pathway[4]. This resulted in a threefold increase of iron content in REPS1 fibroblasts compared to controls suggesting that REPS1 mutations caused a deregulation of iron homeostasis in patient 2, possibly via abnormal endocytosis.

Labile iron overload is known to induce an oxidative stress by Fenton reaction. Oxyblot of cultured fibroblasts from patient 2 detected a slight increase of protein oxidation in low iron conditions (−FAC) but a major increase in high iron conditions (+FAC). Adding FAC to the culture medium increased protection against free radical injury in controls but not in patient 2 fibroblasts suggesting that the maximum level of protection was already achieved in basal conditions.

Transduction of the wt REPS1 cDNA returned iron content of patient 2 fibroblasts to control values confirming that REPS1 variations were indeed responsible for iron overload. Hence, REPS1 mutations cause NBIA via a hitherto unreported mechanism impairing endosome recycling.

CRAT, Involved in CoA Biosynthesis, is a Novel Disease Gene in NBIA

SNP genotyping and exome sequencing in patient 1, born to first cousins parents, identified a homozygous c.962G>A variation in the carnitine acetyltransferase gene (CRAT) altering a highly conserved amino acid residue (p.Arg321His) and predicted to be deleterious. Sanger sequencing confirmed that the variation co-segregated with the disease in the family and was absent from 110 NBIA patients and 200 control chromosomes. CRAT belongs to the group of carnitine acyltransferases that catalyze the reversible transfer of acyl groups between carnitine and coenzyme A (CoA) and regulate acylCoA/CoA ratio. CRAT also plays a crucial role in transport of fatty acids for β-oxidation[6]. Western blot analyses failed to detect the CRAT protein in patient's fibroblasts and analysis of its crystal structure revealed that Arg321, the first residue of a α helix, is involved in H-bonds with several surrounding amino acids that were likely disrupted by the Arg321His change and expected to destabilize the protein.

β-oxidation of U-$^{13}C_{16}$ palmitate in cultured fibroblasts of patient 1 detected decreased levels of C2 compared to control suggesting a reduced β-oxidation. Consistently, incorporation of U-$^{13}C_{16}$ palmitate into citrate and other Krebs cycle intermediates was markedly reduced in patient 1 compared to control fibroblasts (not shown). Consistently, siRNA extinction of CRAT gene expression followed by β-oxidation of labeled palmitoyl-CoA in HeLa cells resulted in a marked decrease of C4 and C2 acylcarnitine derivatives compared to controls, a pattern similar to that observed in cultured fibroblasts of patient 1. Conclusive evidence for the disease causing nature of the CRAT variation was eventually provided by lentiviral transduction of wild-type (wt) human CRAT cDNA in patient 1 fibroblasts followed by the shift of the palmitoyl-CoA β-oxidation profile towards control values.

No other disease causing variant was found and a homozygous c.836G>A acyl-CoA thioesterase 8 (ACOT8) variation (p.Trp279*) was excluded as siRNA extinction of ACOT8 failed to alter palmitoyl-CoA β-oxidation while over-expression of wt ACOT8 cDNA failed to restore normal palmitoyl-CoA β-oxidation.

Iron Content in Fibroblasts of NBIA Patients

When grown in low iron conditions (no FAC and no FBS), cultured fibroblasts showed slightly elevated iron contents in case of biallelic mutations in CRAT, C19ORF12 and FA2H, but not PANK2 and PLA2G6. After a 3 day incubation with FAC, all NBIA fibroblasts exhibited a major cellular iron increase (10 to 30-fold change) while control fibroblasts displayed a 8-fold change ($P<0.001$). This indicates that none of patients' fibroblasts properly regulated iron uptake in NBIA possibly via abnormal endocytosis.

Iron Homeostasis in Cultured Fibroblasts of NBIA Patients

Transferrin receptor (TFRC) mRNAs were quantified by digital droplet PCR in control and NBIA fibroblasts grown in a Tf-free DMEM medium (no FBS, +/−FAC). TFRC mRNA ratios in low (−FAC) vs high iron conditions (+FAC) were relatively similar in controls and NBIA patients (PANK2, PLA2G6, FA2H, C19ORF12, REPS1 and CRAT), suggesting a normal down regulation of TFRC transcripts in high iron conditions.

Similarly, Western blot analyses of cultured fibroblasts grown in low iron conditions (−FAC) detected relatively similar levels of IRP1 and IRP2 in NBIA and controls but a consistent increase of H- and L-ferritins (FTH and FTL respectively) in patients fibroblasts, reflecting iron overload. In high iron conditions (+FAC), low levels of IRP1, IRP2 and TfR1 limited iron uptake in control cells while H- and L-ferritin increased. Most interestingly, however, TfR1 levels failed to decrease in cultured fibroblasts of NBIA patients compared to controls while IRP1, IRP2 and ferritin levels changed according to controls. The same was observed with FBXLS, an iron-sensor protein reflecting size of the labile iron pool. Down regulation of TfR1 normally results from the combined decrease of TFRC transcripts and degradation of TfR1 protein by lysosome. Since pre-translational regulation of TfR1 was unaffected in NBIA, our results suggest the existence of a non-canonical, post-translational regulation of TfR1 and its alteration in NBIA fibroblasts. Since we consistently observed increased amounts of LC3B-II in NBIA fibroblasts grown in high iron conditions, our results are consistent with a deficient targeting of TfR1/autophagosome to lysosomes with subsequent decrease of TfR1 degradation by autophagy in NBIA.

Tf and TfR1 Recycling and Trafficking in NBIA Fibroblasts

We examined Tf recycling by confocal microscopy using Tf-RED in NBIA fibroblasts. Monitoring perinuclear immunofluorescence intensity after a 30 min Tf-RED pulse followed by chase in control fibroblasts showed a rapid decrease of Tf staining ascribed to Tf recycling. By contrast, Tf recycling was significantly delayed in NBIA fibroblasts as the Tf signal aggregated in the vicinity of nuclei and failed to decline after the Tf-RED pulse with a significant delay of 10 min and longer. These results are in agreement with the role of REPS1 in receptor-mediated endocytosis and endosome recycling and suggest that other NBIA mutations also affect endosome recycling.

In control cells, Tf and TfR1 colocalized and were evenly distributed in the cytosol. They partly colocalized with RAB11A, a marker of the recycling compartment or were degraded by lysosome as Tf also colocalized with LAMP2, a lysosomal marker.

Interestingly, Tf and TfR1 signals were more intense and mostly present in a perinuclear region in NBIA fibroblasts compared to controls. RAB11A signal was also increased and focusing on this region detected a large and bright spot suggestive of a blockade in perinuclear endosome recycling. We therefore questioned whether TfR1 accumulation in NBIA fibroblasts was related to its defective degradation by lysosome. In fact, Tf/LAMP2 positive structures were decreased in NBIA fibroblasts paralleling the increase of LC3B-II detected by Western blot in NBIA fibroblasts grown in high iron conditions. Moreover, all NBIA fibroblasts showed enlarged lysosomes with doughnut shape, an observation consistent with an impaired lysosome degradation of TfR1.

Concomitant increased levels of TfR1 and ferritin observed either in low or high iron condition is paradoxical as stored iron should down regulate TfR1 levels and metal import. Whereas we detected abnormal TfR1 recycling and its impaired lysosome degradation we questioned whether the increased steady-state level of TfR1 was also related to abnormally high TfR1 uptake. To address this issue, next generation imaging flow cytometry was used to quantify TfR1. This analysis showed increased amounts of TfR1 at the cell surface of NBIA fibroblasts compared to controls and quantification using the IDEA software revealed a significantly increased TfR1 signal in patients' fibroblasts. These results suggest that despite iron overload, NBIA patient fibroblasts fail to down regulate metal uptake by TfR1.

TfR1 Palmitoylation in NBIA Fibroblasts

TfR1 is post-transitionally modified by covalent attachment of S-acyl, palmitate being the predominant fatty acid, via thio-ester bonds to $Cys^{62}$ and $Cys^{67}$ [14]. Remembering that i) increased palmitoylation has been shown to decrease TfR1 amount at the cell surface and its endocytosis[15] and ii) acetyl-CoA is the sole donor of acetyl groups for acetyl transferases, we hypothesized that CoA deficiency related to PANK2 and CRAT mutations could reduce TfR1 palmitoylation. We investigated TfR1 palmitoylation in PANK2 and CRAT deficient fibroblasts using fatty acyl exchange chemistry method and observed a significant decrease compared to controls suggesting that impaired CoA biosynthesis could directly alter TfR1 palmitoylation. Interestingly, a major palmitoylation defect was also observed in other NBIA (PLA2G6, FA2H, C19ORF12 and REPS1), the defect being particularly severe in C19ORF12 and PLA2G6 fibroblasts. Artesunate is known to inhibit liver and ovarian cancer growth by disrupting iron cellular homeostasis via an induction of TfR1 palmitoylation and a reduction of its cell-surface levels[15]. Control and NBIA fibroblasts were therefore treated by 25 µM artesunate for 48 h that indeed enhanced TfR1 palmitoylation. Interestingly, ferritin (FTH) steady state levels were decreased by artesunate treatment in control and NBIA fibroblasts reflecting a decrease of iron content as previously shown.

Discussion

Studying a series of known and hitherto unreported disease genes, we report here on increased levels and abnormal recycling of TfR1 as a common feature in NBIA. As numerous other membrane receptors, TfR1, with Tf-bound iron, is internalized via clathrin-mediated endocytosis and subsequent endosomal trafficking allows its recycling to the membrane. Iron stored in uncoated vesicles is released in the cytosol after acidification of the vesicles that occurs before their fusion with endosome, mediated by the binding of REPS1 to RalBP1. We hypothesized that REPS1 mutations could impair REPS1-Rab11FIP2 binding and consequently alter the turnover of iron resulting in iron overload. Consistent with this hypothesis we observed an increase of iron content and a paradoxically increased steady state level of TfR1 in cultured fibroblasts of a patient carrying REPS1 mutations but also in patients carrying other NBIA gene mutations, namely CRAT, PANK2, PLA2G6, FA2H and C19ORF12. Hence, whatever the disease gene, all NBIA gave rise to increased iron load with increased TfR1 amount and delayed Tf/TfR1 recycling. Interestingly, abnormal TfR1 recycling has been already reported in phospholipase A2 deficient models as phospholipase A2 antagonists inhibit Tf-TfR1 recycling at the levels of both early sorting and late recycling of endosomes[16,17]. Taken together these results point toward defective endosome recycling as a common mechanism in NBIA. Based on this study, we suggest considering NBIA as a trafficking disease triggered by impairment of TfR1 recycling.

Increased levels of TfR1 in the context of iron overload is paradoxical as stored iron should normally down regulate TfR1. It is worth noting that the post-transcriptional regulation of TfR1 by IRP/IRE properly functioned in NBIA fibroblasts as TFRC transcripts were normally down regulated in high iron conditions. Therefore, the abnormally high level of TfR1 reported here is suggestive of a post-translational dysfunction in NBIA fibroblasts. We ascribe this anomaly to impaired palmitoylation of the receptor as a common consequence of the various disease causing mutations tested. Several data argue for a palmitoylation defect in NBIA: i) it is worth remembering that CRAT and PANK2 are involved in the production of CoA required for palmitoylation and we detected a defect of palmitate β-oxidation in fibroblasts carrying CRAT mutations; ii) metabolic profiling in PANK2 fibroblasts previously showed decreased amount of palmitic acid and reduced lipid biosynthesis[18]; iii) COASY fibroblasts are also known to display reduced amounts of acetyl and total CoA expected to decrease palmitic acid[19]; iv) similarly, mice deficient in phospholipase A2 displayed reduction in palmitate β-oxidation[20]; v) another NBIA gene, FA2H encodes a fatty acid hydroxylase transforming fatty acid into 2-hydroxy fatty acid but no metabolic studies have been hitherto performed in FA2H patients; vi) finally, impaired CoA synthesis related to PANK2 mutations have been shown to induce alterations in histone and tubulin acetylation[21]. Taken together, our data and previous studies support the view that palmitoylation of the TfR1 is altered in NBIA.

TfR1 has long known to be post-translationally modified by S-acylation, including palmitoylation, as palmitate (C16:0) is the major lipid incorporated into S-acylated proteins. Intracellular iron content depends from TfR1 palmitoylation as mutations of $Cys^{62}$ and $Cys^{67}$ that are the major sites of TfR1 palmitoylation resulted in iron overload[14] and as dihydroartesunate treatment, increasing palmitoylation, reduces iron amount[15]. However, the consequences of TfR1 palmitoylation level on its uptake are controversial. Indeed, it has been claimed that decreased TfR1 palmitoylation increases its uptake[14] but further studies did no detect modification of TfR1 uptake depending on palmitoylation modification[15,22]. These discrepancies could probably be related to the time at which TfR1 uptake was measured in these various studies. Modifications of S-acylation sites of TfR1 by mutations of $Cys^{62}$ and $Cys^{67}$ doesn't hamper its recycling[14] whereas we observed abnormal TfR1 recycling in NBIA. A large number of proteins are palmitoylated including proteins of endosome recycling. Therefore, the abnormal TfR1 recycling in NBIA should be related to decreased palmitoylation of other, yet unknown, endosomal proteins that could also play a role in the pathophysiology of the disease. In keeping with this, we have also found preliminary evidence of abnormal lysosomal degradation in NBIA as Tf/TfR1 either accumulated in lysosomes of CRAT and PLA2G6 fibroblasts or were decreased in REPS1, PANK2, FA2H and C19ORF12 cells. Finally, PLA2G6 has been shown to be involved in trans-Golgi network to plasma membrane[23] and to regulate morphology and intraorganellar traffic in the endoplasmic reticulum-Golgi intermediate compartment[24]. TfR1 normally recycles at least 100 times or more during its life time and undergoes several acylation/deacylation cycles as S-acylation is reversible[25]. Because S-acyl transferases are exclusively membrane-associated and mainly localized to ER and Golgi membranes[26], one can hypothesize that abnormal recycling caused by REPS1 mutations should slow down TfR1 trafficking and reduce its palmitoylation. Finally, as C19ORF12 is a mitochondrial protein[27] that does not include a S-acyl transferase domain, one can hypothesize that this protein is involved in fatty acid metabolism.

Palmitoylation is a rapid mechanism of post-translational regulation. Indeed, the half-life of [³H]palmitate incorporated into N-Ras is 20 min[28]. Considering that the post-transcriptional down-regulation of TfR1 in high iron conditions requires several hours[29] and that the half-life of TfR1 protein is more than 24 h[30], post-translational regulation of TfR1 by palmitoylation could represent an alternative to rapidly modulate cellular iron content, a regulation that might be impaired or challenged in NBIA.

Abnormal palmitoylation has seldom been reported in genetic diseases and only in relation with mutations in acylation enzymes. Most of them are neurological or neurophyschiatric disorders, including Huntington's disease, Alzheimer's disease, schizophrenia, bipolar disorder, X-linked mental retardation, ceroid lipofuscinosis[31], and models of Parkinson disease[22], highlighting the importance of palmitoylation for normal neuronal function. Yet, why mutations in NBIA genes which are ubiquitously expressed, resulted in neurological diseases only remains unanswered. At least 23 palmitoyl transferases (PAT) are expressed in brain and display various patterns of expression and not all their substrates have been identified. One could hypothesize that the brain specific clinical expression of NBIA may result from hitherto unknown TfR1-specific PAT(s). Identification of the(se) PAT(s) should help better understanding the disease mechanism.

Finally, we show that artesunate improved TfR1 palmitoylation in NBIA fibroblasts and decreased ferritin steady state level, an indicator of iron content. Artesunate, a derivative or artemisinin, widely used as antimalarial drug[32], also shows potent anticancer activities in a variety of human cancer cells[33]. Artemisinin has long been known to induce iron depletion that is toxic for cancer cells, and is used to fight *P. falciparum*, the malaria parasite which requires large amounts of iron. Several millions of patients have received artemisinin for malaria treatment with very few side effects. Yet, neither its safety nor its pharmacokinetics in neurodegenerative disorders have been established. We suggest giving consideration to artemisinin and other drugs increasing TfR1 palmitoylation as possible ways towards therapeutical trials in NBIA as well as in other more frequent neurodegenerative diseases such as Parkinson disease associated with brain iron accumulation.

EXAMPLE 2 (FIG. 1): ABNORMAL IRON CONTENT AND HOMEOSTASIS IN CULTURED FIBROBLASTS OF NBIA SUBJECTS

The FIG. 1 shows abnormal iron overload and TfR1 deregulation in fibroblasts of subject with PLA2G6 mutations (PLA2G6-2, c.109C>T (p.Arg37*) and c.386T>C.

REFERENCES

Throughout this application, various references describe the state of the art to which this invention pertains. The disclosures of these references are hereby incorporated by reference into the present disclosure.

1. Meyer, E., Kurian, M. A. & Hayflick, S. J. Neurodegeneration with Brain Iron Accumulation: Genetic Diversity and Pathophysiological Mechanisms. Annu Rev Genomics Hum Genet 16, 257-79 (2015).
2. Jaberi, E. et al. Identification of mutation in GTPBP2 in patients of a family with neurodegeneration accompanied by iron deposition in the brain. Neurobiol Aging 38, 216 e11-8 (2016).
3. Lane, D. J. et al. Cellular iron uptake, trafficking and metabolism: Key molecules and mechanisms and their roles in disease. Biochim Biophys Acta 1853, 1130-44 (2015).
4. Sohn, Y. S. et al. The role of endocytic pathways in cellular uptake of plasma non-transferrin iron. Haematologica 97, 670-8 (2012).
5. Gray, N. K. & Hentze, M. W. Iron regulatory protein prevents binding of the 43S translation pre-initiation complex to ferritin and eALAS mRNAs. EMBO J 13, 3882-91 (1994).
6. Jogl, G., Hsiao, Y. S. & Tong, L. Structure and function of carnitine acyltransferases. Ann N Y Acad Sci 1033, 17-29 (2004).
7. Dergai, O. et al. Intersectin 1 forms complexes with SGIP1 and Reps1 in clathrin-coated pits. Biochem Biophys Res Commun 402, 408-13 (2010).
8. Krieger, J. R. et al. Identification and selected reaction monitoring (SRM) quantification of endocytosis factors associated with Numb. Mol Cell Proteomics 12, 499-514 (2013).
9. Xu, J. et al. Cloning, expression and characterization of a novel human REPS1 gene. Biochim Biophys Acta 1522, 118-21 (2001).
10. Yamaguchi, A., Urano, T., Goi, T. & Feig, L. A. An Eps homology (EH) domain protein that binds to the Ral-GTPase target, RalBP1. J Biol Chem 272, 31230-4 (1997).
11. Cullis, D. N., Philip, B., Baleja, J. D. & Feig, L. A. Rab11-FIP2, an adaptor protein connecting cellular components involved in internalization and recycling of epidermal growth factor receptors. J Biol Chem 277, 49158-66 (2002).
12. Boissel, L., Fillatre, J. & Moreau, J. Identification and characterization of the RLIP/RALBP1 interacting protein Xreps1 in Xenopus laevis early development. PLoS One 7, e33193 (2012).
13. Kaplan, J., Jordan, I. & Sturrock, A. Regulation of the transferrin-independent iron transport system in cultured cells. J Biol Chem 266, 2997-3004 (1991).
14. Alvarez, E., Girones, N. & Davis, R J Inhibition of the receptor-mediated endocytosis of diferric transferrin is associated with the covalent modification of the transferrin receptor with palmitic acid. J Biol Chem 265, 16644-55 (1990).
15. Ba, Q. et al. Dihydroartemisinin exerts its anticancer activity through depleting cellular iron via transferrin receptor-1. PLoS One 7, e42703 (2012).
16. de Figueiredo, P. et al. Inhibition of transferrin recycling and endosome tubulation by phospholipase A2 antagonists. J Biol Chem 276, 47361-70 (2001).
17. Doody, A. M., Antosh, A. L. & Brown, W. J. Cytoplasmic phospholipase A2 antagonists inhibit multiple endocytic membrane trafficking pathways. Biochem Biophys Res Commun 388, 695-9 (2009).
18. Leoni, V. et al. Metabolic consequences of mitochondrial coenzyme A deficiency in patients with PANK2 mutations. Mol Genet Metab 105, 463-71 (2012).
19. Dusi, S. et al. Exome sequence reveals mutations in CoA synthase as a cause of neurodegeneration with brain iron accumulation. Am J Hum Genet 94, 11-22 (2014).
20. Song, H. et al. Mice deficient in group VIB phospholipase A2 (iPLA2gamma) exhibit relative resistance to obesity and metabolic abnormalities induced by a Western diet. Am J Physiol Endocrinol Metab 298, E1097-114 (2010).
21. Siudeja, K. et al. Impaired Coenzyme A metabolism affects histone and tubulin acetylation in Drosophila and human cell models of pantothenate kinase associated neurodegeneration. EMBO Mol Med 3, 755-66 (2011).
22. Senyilmaz, D. et al. Regulation of mitochondrial morphology and function by stearoylation of TFR1. Nature 525, 124-8 (2015).
23. Schmidt, J. A., Kalkofen, D. N., Donovan, K. W. & Brown, W. J. A role for phospholipase A2 activity in membrane tubule formation and TGN trafficking. Traffic 11, 1530-6 (2010).
24. Ben-Tekaya, H., Kahn, R. A. & Hauri, H. P. ADP ribosylation factors 1 and 4 and group VIA phospholipase A(2) regulate morphology and intraorganellar traffic in the endoplasmic reticulum-Golgi intermediate compartment. Mol Biol Cell 21, 4130-40 (2010).
25. Zaliauskiene, L. et al. Down-regulation of cell surface receptors is modulated by polar residues within the transmembrane domain. Mol Biol Cell 11, 2643-55 (2000).
26. Chamberlain, L. H. & Shipston, M. J. The physiology of protein S-acylation.
Physiol Rev 95, 341-76 (2015).
27. Hartig, M. B. et al. Absence of an orphan mitochondrial protein, c19orf12, causes a distinct clinical subtype of neurodegeneration with brain iron accumulation. Am J Hum Genet 89, 543-50 (2011).
28. Magee, A. I., Gutierrez, L., McKay, I. A., Marshall, C. J. & Hall, A. Dynamic fatty acylation of p21N-ras. EMBO J 6, 3353-7 (1987).
29. Mullner, E. W. & Kuhn, L. C. A stem-loop in the 3' untranslated region mediates iron-dependent regulation of transferrin receptor mRNA stability in the cytoplasm. Cell 53, 815-25 (1988).

30. Zaliauskiene, L. et al. Inhibition of T cell responses by transferrin-coupled competitor peptides. Immunol Res 26, 77-85 (2002).
31. Chavda, B., Arnott, J. A. & Planey, S. L. Targeting protein palmitoylation: selective inhibitors and implications in disease. Expert Opin Drug Discov 9, 1005-19 (2014).
32. Efferth, T. & Kaina, B. Toxicity of the antimalarial artemisinin and its dervatives. Crit Rev Toxicol 40, 405-21 (2010).
33. Lai, H. C., Singh, N. P. & Sasaki, T. Development of artemisinin compounds for cancer treatment. Invest New Drugs 31, 230-46 (2013).
34. Mutterer, J. & Zinck, E. Quick-and-clean article figures with FigureJ. J Microsc 252, 89-91 (2013).
35. Barbeito, A. G., Levade, T., Delisle, M. B., Ghetti, B. & Vidal, R. Abnormal iron metabolism in fibroblasts from a patient with the neurodegenerative disease hereditary ferritinopathy. Mol Neurodegener 5, 50 (2010).
36. Moura, I. C. et al. A neutralizing monoclonal antibody (mAb A24) directed against the transferrin receptor induces apoptosis of tumor T lymphocytes from ATL patients. Blood 103, 1838-45 (2004).
37. Hanein, S. et al. TMEM126A is a mitochondrial located mRNA (MLR) protein of the mitochondrial inner membrane. Biochim Biophys Acta 1830, 3719-33 (2013).

The invention claimed is:

1. A method of treating neurodegeneration with brain iron accumulation (NBIA) in a subject in need thereof comprising administering to the subject a therapeutically effective amount of a drug increasing transferrin receptor 1 (TfR1) palmitoylation, wherein the drug is selected from the group consisting of artesunate, a prodrug of artesunate and artemisinin.

2. The method of claim 1 wherein the NBIA results from a disease gene selected from PANK2, PLA2G6, COASY, FA2H, ATP13A2, C2orf37, WDR45, C19ORFf12, CP, FTL, GTPBP2, CRAT and REPS1.

3. The method of claim 1 wherein the NBIA is pantothenic kinase-associated neurodegeneration, infantile neuroaxonal dystrophy, atypical neuroaxonal dystrophy, mitochondrial-membrane protein-associated neurodegeneration, beta-propeller protein-associated neurodegeneration, aceruloplasminemia, fatty acid hydroxylase-associated neurodegeneration, neuroferritinopathy, Woodhouse-Sakati syndrome, or coasy protein-associated neurodegeneration.

4. A method of treating neurodegeneration with brain iron accumulation (NBIA) in a subject in need thereof comprising administering to the subject a therapeutically effective amount of artesunate, wherein said therapeutically effective amount is sufficient to increase transferrin receptor 1 (TfR1) palmitoylation in cells of the subject.

* * * * *